Dec. 17, 1963 S. D. McGREDY IV Plant Pat. 2,327
ROSE PLANT
Filed Nov. 16, 1962
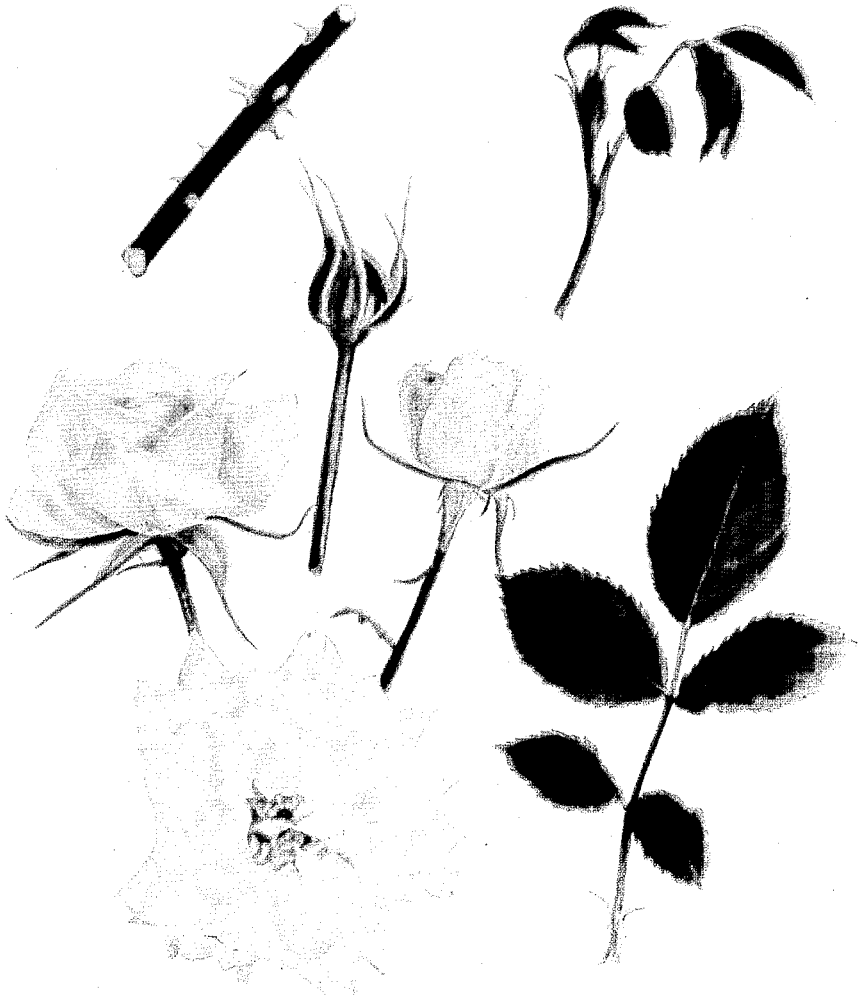
Inventor.
Samuel D. McGredy, IV
By: Pobb & Pobb
Attorneys.

United States Patent Office

Plant Pat. 2,327
Patented Dec. 17, 1963

2,327
ROSE PLANT

Samuel D. McGredy IV, Portadown, Ireland, assignor to Jackson & Perkins Company, Newark, N.Y., a corporation of New York Filed Nov. 16, 1962, Ser. No. 238,311
1 Claim. (Cl. Plt.—28)

The present invention relates to a new and distinct variety of rose plant of the floribunda class, which was originated by me by crossing the variety known as "Spartan" (U.S. Plant Patent No. 1,357) with the variety known as "Tzigane" (U.S. Plant Patent No. 1,188).

The primary objective of this breeding was to produce a new rose variety which bears flowers comparable to those of the parent variety "Spartan," but which have higher color. While the result did not achieve the sharp flower color of the parent variety "Tzigane," it did achieve a substantial accentuation of the "Spartan" flower color, along with other desirable improvements, as evidenced by the following unique combination of characteristics which are outstanding in the new variety and which distinguish it from its parents, as well as from all other varieties of which I am aware:

(1) A medium low habit of plant growth which is unusual in a seedling of "Spartan";

(2) Foliage similar to that of "Spartan";

(3) A distinctive peduncle color corresponding to Biscay Green, lightly overcast with Ocher Red;

(4) Excellent buds of ovoid form;

(5) Flowers of good size, averaging about 4 inches in diameter; and (6) A distinctive and attractive Scarlet Red general color tonality of the flowers.

Asexual reproduction of my new variety by budding, as performed at Newark, New York, U.S.A., and also at Pleasanton, California, U.S.A., shows that the aforementioned characteristics come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
*Seed parent.*—"Spartan."
*Pollen parent.*—"Tzigane."
Classification:
*Botanic.*—Floribunda.
*Commercial.*—Floribunda.

*Flower*

(Observations made from specimens grown outdoors at Newark, New York, U.S.A., in the early morning during the early part of the month of July.)
Blooming habit: Recurrent—continuous.
Bud:
*Size.*—Large.
*Form.*—Ovoid; is not affected by wet or hot weather.
*Color.*—When sepals first divide—Eugenia Red, Plate 13. When petals begin to unfurl—Scarlet-Red, Plate 1, very lightly overcast with Scarlet, Plate 1. When half-blown—inside of petals: Scarlet Red, Plate 1, lightly overcast with Scarlet, Plate 1; reverse of petals: Scarlet, Plate 1, lightly overcast with Scarlet Red, Plate 1.
*Sepals.*—Slightly branched; curl back when petals begin to unfurl. Color—inside: Light Fluorite Green, Plate 32; outside: Deep Dull Yellow-Green (1), Plate 32.
*Calyx.*—Color—Biscay Green, Plate 17. Shape—funnel. Size—small. Aspect—smooth. Odor when rubbed—none.
*Peduncle.*—Length — medium. Aspect — smooth. Strength—Erect; slender. Color—Biscay Green, Plate 17, with lower half of peduncle lightly overcast with Ocher Red, Plate 27.
*Opening.*—Opens up well; is not affected by adverse weather conditions.
Bloom:
*Size.*—Large. Average size when fully expanded—4 inches.
*Borne.*—Both singly and several together.
*Stems.*—Medium length; normal strength
*Form (when first open).*—Cupped. *Permanence*—retains its form to the end, but outer petals curl back.
*Petalage.*—Double (full but open center). Number of petals under normal conditions—from 30 to 35.
*Color.*—Center of flower—Scarlet Red, Plate 1. Outer petals—Scarlet Red, Plate 1, lightly overcast with Rose Red, Plate 12. Base of petals (aiglet)—Marguerite Yellow, Plate 30. Inside of petals—Scarlet Red, Plate 1, very lightly overcast with Scarlet, Plate 1. Reverse of petals—Rose Red, Plate 1, very lightly overcast with Scarlet, Plate 1. General tonality from a distance—Scarlet, Plate 1.
*Discoloration.*—General tonality at end of first day—Scarlet Red, Plate 1. Second day—Scarlet Red, Plate 1. Third day—Scarlet Red, Plate 1, very lightly overcast with Scarlet, Plate 1.
Petals:
*Texture.*—Leathery; is not affected by wet or hot weather.
*Appearance.*—Inside—santiny. Outside—shiny.
*Form.*—Oval.
*Arrangement.* — Imbricated (regularly arranged shingle-like).
*Petaloids in center.*—Few; small.
*Persistance.*—Drop off cleanly.
*Fragrance.*—Moderate. Nature—tea (average hybrid tea scent).
*Lasting quality.*—On plant—long. On cut flower—long.

*Genital organs*

Stamens, Anthers: Medium size; many; regularly arranged around styles. Color—Buff-Yellow, Plate 4.
Stamens, Filaments (threads): Medium length. Color—Deep Rose Pink, Plate 12.
Pollen: Color—Maize Yellow, Plate 4.
Styles: Bunched; uneven length; medium length; thin.
Stigmas: Color—Cream Buff, Plate 30.
Ovaries: All enclosed in calyx.
Hips: None.
Seeds: None.

*Plant*

Form: Bush.
Growth: Vigorous; upright; medium low (ranging from about 2 feet to 2½ feet).
Foliage: Compound of 3–5 leaflets.
*Size.*—Medium.
*Quantity.*—Normal.
*Color.*—New foliage—upper side: Van Dyke Red, Plate 13; under side: Yellowish Oil Green, Plate 5. Old foliage—upper side: Spinach Green, Plate 5; under side: Light Cree Green, Plate 31.

*Shape.*—Oval.

*Texture.*—Upper side—leathery. Under side—smooth.

*Ribs and veins.*—Ordinary.

*Edge.*—Serrated (saw-toothed).

*Serration.*—Both double and single; small.

*Leaf stem.*—Color—Bice Green, Plate 17. Under side—rough.

*Stipules.*—Medium length; bearded.

Wood:

*New wood.*—Color—Parrot Green, Plate 6, very lightly overcast with Van Dyke Red, Plate 13. Bark—smooth.

*Old wood.*—Color—Empire Green, Plate 32. Bark—smooth.

Thorns:

*Thorns.*—Quantity—on main stalks from base: ordinary; on laterals from stalk: ordinary. Form—narrow base; medium length; hooked downward.

Color (when young)—Eugenia Red, Plate 13. Position—irregular.

*Prickles.*—Quantity—on main stalks: none; on laterals—none.

*Short needles.*—Quantity—on main stalks: none; on laterals—none.

I claim:

A new and distinct variety of rose plant of the floribunda class, substantially as herein shown and described, characterized particularly as to novelty by the unique combination of a medium low habit of plant growth, foliage similar to that of the variety "Spartan" (U.S. Plant Patent No. 1,357), a distinctive peduncle color corresponding to Biscay Green, lightly overcast with Ocher Red, excellent buds of ovoid form, good flower size, and a distinctive and attractive Scarlet Red general color tonality of the flowers.

No references cited.